United States Patent [19]
Randers-Pehrson et al.

[11] Patent Number: 5,818,054
[45] Date of Patent: Oct. 6, 1998

[54] SUBSTANCE DETECTION DEVICE USING MONOENERGETIC NEUTRONS

[75] Inventors: Gerhard Randers-Pehrson, Yonkers; David Brenner, New York, both of N.Y.

[73] Assignee: Radio Programmes Corp., Garrison, N.Y.

[21] Appl. No.: 841,113

[22] Filed: Apr. 29, 1997

Related U.S. Application Data

[60] Provisional application No. 60/016,578 Apr. 30, 1996.

[51] Int. Cl.[6] .......................... G01N 23/09; G01N 33/22
[52] U.S. Cl. .............................. 250/390.04; 250/390.02; 250/390.06; 250/391; 250/392
[58] Field of Search .................. 250/390.01, 390.02, 250/390.04, 390.06, 390.1, 391, 392, 393, 394

[56] References Cited

U.S. PATENT DOCUMENTS

| | | |
|---|---|---|
| 4,575,634 | 3/1986 | Redler et al. ............... 250/390.04 X |
| 5,124,554 | 6/1992 | Fowler et al. . |
| 5,142,153 | 8/1992 | Gomberg . |
| 5,200,626 | 4/1993 | Schultz et al. ............... 250/390.04 |
| 5,278,418 | 1/1994 | Broadhurst . |
| 5,440,136 | 8/1995 | Gomberg . |
| 5,479,023 | 12/1995 | Bartle ............... 250/390.04 |
| 5,606,167 | 2/1997 | Miller ............... 250/390.04 |

OTHER PUBLICATIONS

Anthony Fainberg, "Explosives Detection for Aviation Security", *Science* vol. 255, 1992, pp. 1531–1537.

*Primary Examiner*—Edward J. Glick
*Attorney, Agent, or Firm*—Frommer, Lawrence & Haug LLP

[57] ABSTRACT

A method and apparatus for non-invasively determining the internal composition of objects are disclosed. The object of interest is probed with low energy, monoenergetic narrow beams of fast neutrons. The object is generally placed on a conveyor belt which is positioned between the accelerator and the detectors. Detectors, positioned at radial angles corresponding to the resonance energy levels of certain preselected elements, measure the neutrons that are not absorbed or scattered by the elements in the object and thus pass straight through the object. The information obtained from the detectors can then be used for subsequent tomographic reconstruction.

25 Claims, 9 Drawing Sheets

NITROGEN ATTENUATOR

◇ IS NITROGEN GAS DETECTOR AT ANGLE CORRESPONDING TO 433.6 KeV NEUTRONS (ON BOTH NITROGEN AND OXYGEN RESONANCES)
□ IS OXYGEN GAS DETECTOR AT ANGLE CORRESPONDING TO 422 KeV NEUTRONS (ON OXYGEN BUT OFF NITROGEN RESONANCE)
× IS DEUTERIUM GAS DETECTOR AT ANGLE CORRESPONDING TO 500 KeV INCIDENT NEUTRONS (OFF BOTH NITROGEN AND OXYGEN RESONANCES)

FIG. 6B

OXYGEN ATTENUATOR

◇ IS NITROGEN GAS DETECTOR AT ANGLE CORRESPONDING TO 433.6 KeV NEUTRONS (ON BOTH NITROGEN AND OXYGEN RESONANCES)
□ IS OXYGEN GAS DETECTOR AT ANGLE CORRESPONDING TO 422 KeV NEUTRONS (ON OXYGEN BUT OFF NITROGEN RESONANCE)
✕ IS DEUTERIUM GAS DETECTOR AT ANGLE CORRESPONDING TO 500 KeV INCIDENT NEUTRONS (OFF BOTH NITROGEN AND OXYGEN RESONANCES)

FIG. 6C

◇ IS NITROGEN GAS DETECTOR AT ANGLE CORRESPONDING TO 433.6 KeV NEUTRONS (ON BOTH NITROGEN AND OXYGEN RESONANCES)
□ IS OXYGEN GAS DETECTOR AT ANGLE CORRESPONDING TO 422 KeV NEUTRONS (ON OXYGEN BUT OFF NITROGEN RESONANCE)
× IS DEUTERIUM GAS DETECTOR AT ANGLE CORRESPONDING TO 500 KeV INCIDENT NEUTRONS (OFF BOTH NITROGEN AND OXYGEN RESONANCES)

FIG. 6D

SUBSTANCE DETECTION DEVICE USING MONOENERGETIC NEUTRONS

CROSS-REFERENCE TO RELATED APPLICATION

This application claims the benefit of U.S. Provisional application Ser. No. 60/016,578, filed Apr. 30, 1996.

BACKGROUND OF THE INVENTION

1. Field of the Invention

This invention relates generally to methods and apparatus for non-invasively determining the composition of objects, particularly closed containers or otherwise inaccessible objects. More particularly, the present invention relates to a method and apparatus that uses neutron scattering to identify the existence of particular elements that are abundant in explosives.

2. Description of the Invention

The need exists for a rapid, safe, accurate and non-intrusive inspection system for determining the presence of certain elements in objects such as suitcases and luggage. This need is especially great for identifying the presence of explosives or explosive devices in suitcases or any other parcel to be brought upon an airplane.

It is well known that essentially all explosives are both oxygen and nitrogen rich. One way to detect concealed explosives is to use penetrating radiation, such as neutrons, and to detect the interaction of the neutrons with oxygen and nitrogen atoms.

Uncharged particles, such as neutrons and photons (gamma rays) have the potential to penetrate relatively large dense objects and to identify particular elements of interest. Several detection devices have utilized the absorption and/or scattering patterns of the neutrons or photons as they interact with certain elements present in the object being inspected.

A number of the processes used to detect concealed explosives have irradiated suspicious containers with thermal neutrons or, alternatively, with pulsed fast neutrons. Both systems measure the emitted gamma rays produced by the absorption of a neutron by the element of interest. The techniques have involved thermal neutron analysis (TNA) described by R. R. Smith in *Substance Detection Systems*, Proc. SPIE 2092, pp. 301–306 (1994) and pulsed fast neutron analysis (PFNA) described in Nucl. Inst. and Meth. B 79: 593–596 (1993) by Z.P. Sawa.

In thermal neutron analysis systems ("TNAS"), very low energy neutrons (at or about 0.025 eV) are employed to bombard a sample under investigation. The nuclei of component atoms capture these neutrons and emit photons which are then detected. A significant problem with this method is that the radioactivity may persist for a period of time presenting a potential health hazard. In addition, TNAS exhibit both poor spatial resolution and poor sensitivity and are generally only potentially practical for detecting relevant quantities of explosives when used in combination with x-ray machines.

Pulsed fast neutron analysis is limited in resolution and detection time due to neutron attenuation and scattering, detector response time, and time correlated effects such as gamma ray scattering. In addition, a complex high-energy pulsed accelerator is needed, in conjunction with time-of-flight systems.

Gamma ray nuclear resonance absorption (GNRA) described in *Substance Detection Systems*, Proc. SPIE 2092, pp. 307–316 (1994), is a method which probes a single element (typically nitrogen) with gamma rays of a particular energy. The gamma rays excite the nitrogen nucleus which promptly returns to its lowest energy state, emitting a cascade of gamma rays in the process. Detecting the cascade signals the presence of nitrogen. This technique can only practically detect a single element, generally nitrogen. Thus, it is far more prone to false alarms than a multi-element detection system which includes, at a minimum, nitrogen and oxygen.

Fast neutron transmission spectroscopy (FNTS) is another nuclear detection method used to identify particular elements of interest. FNTS, as described in Overley J. C. et al., *Nucl. Instr. and Meth.* B99:728–732 (1995) and Sale, K. E., *Substance Detection Systems*, Proc. SPIE 2092, pp. 263–270 (1994), uses a high intensity pulsed polyenergetic neutron beam. An attenuated neutron energy spectrum is assessed by time of flight. There are a number of significant drawbacks to using this inspection system due to the fairly complex high energy pulsed accelerator that is needed in conjunction with a time of flight system. In addition, sensitivity is quite limited because a fairly small decrease in the overall unattenuated signal is sought in a field in which there are significant background signals from neutron scattering. U.S. Pat. No. 5,142,153 to Gomberg, discloses a method and apparatus for detecting the presence of a preselected element in an object such as a suitcase. In this particular system, a neutron beam is directed into the object and the neutrons that are resonantly scattered by the preselected element are measured. Since it is the scattered neutrons that are being measured, banks of detectors are needed at a variety of locations depending on the direction of the scattering. The detectors used are standard neutron detectors containing a neutron responsive material as well as a sensitive material having a resonance at a preselected energy.

U.S. Pat. No. 5,278,418 to Broadhurst describes a method for detecting the presence of oxygen and nitrogen in a container. High energy neutrons are passed through a suitcase. The neutrons that penetrate the object of interest and pass through to the other side are detected. The detectors used are standard neutron detectors. The accelerator focuses a proton beam upon a boron target in order to create the neutron beam. The proton beam is periodically subjected to an energy degrading medium upstream of the neutron generating target in order to modify the energy of the protons and thus to change the energy of the neutrons so that different elements can be detected. A major disadvantage of this approach to changing the energy of the neutron beam is that proton multiple scattering inside the degrading medium produces a non-monoenergetic proton beam and thus a non-monoenergetic neutron beam.

Each of the explosive detector systems described has significant drawbacks or disadvantages. In particular, these devices generally utilize accelerators that produce high energy neutrons with a broad spectrum of energies. The absorption/scattering of neutrons traveling at specific energies are difficult to detect given the large number of neutrons that pass through the object without interaction. Thus, the "fingerprint" generated from the device is extremely small, difficult to analyze, and often leads to significant numbers of false positive or false negative test results. In addition, the accelerator needed to produce the high energy neutron spectrum is large, expensive, and requires extensive protective shielding. Moreover, at these high energies, the neutrons can induce nuclear reactions in the element being scanned and convert the elements of the object into a radioactive form (neutron activation).

"Time-of-flight" detection techniques are frequently employed in PFNA and FNTS to provide energy discrimination to high energy neutron detectors. In time-of-flight detection, pulses of neutrons are directed onto an object. A detector is activated in synchrony with each pulse so as to sample (measure) the scattered or transmitted neutrons on a temporal and hence energetic basis. Due to their complexity, time-of-flight techniques are problematic for large-scale explosive detectors and require a pulsed neutron source, fairly large source/detector geometries (i.e., a long flight path) and sophisticated timing circuitry. The long-term reliability of such systems is particularly uncertain.

The apparatus of the instant invention addresses the problems inherent in other devices and provides a detector system which uses low energy monoenergetic fast neutrons to identify the number and spatial distribution of specific elements in the object being examined. The use of monoenergetic neutrons results in a number of significant advantages over these other methods of explosive detection. The use of low fast-neutron energies requires a comparatively low energy proton beam for the neutron generating reactions. This allows for a small, simple, economical and reliable accelerator system. The generation of low energy fast-neutrons also can allow a correlation between the angle of the neutron beam and the outgoing neutron energy, so that monoenergetic neutron beams can be utilized. Such exact angle/energy correlations disappear at higher energies.

Further, because low-energy fast neutrons are used and time-of-flight analysis is not required, and because the apparatus does not require extensive protective shielding, the physical "footprint" of the equipment is small. Furthermore, because only monoenergetic neutrons are used, which correspond exactly to large resonances in the nitrogen and oxygen interaction cross sections (interaction probabilities), the signal to noise ratio of the system is favorable, leading to high sensitivity and specificity for quantitatively detecting the elements of interest. Furthermore, at there low fast-neutron energies, neutron activation and the subsequent conversion to radioactive elements does not occur with the neutron used in this invention. These and other advantages of the invention will be readily apparent from the drawings, discussion and description which follow.

The contents of any references cited in the specification are hereby incorporated by reference.

SUMMARY OF THE INVENTION

It is thus an object of the invention to provide a novel method for detecting the presence of certain elements in a container or other object. More specifically, it is an object of this invention to provide a novel nuclear detection method and apparatus for detecting the presence of characteristically high levels of oxygen and nitrogen in a region within a container, as a screening technique for determining the presence of an explosive, in parcels and baggage that are transported by passenger aircraft.

The present invention relates to a neutron resonance detector system that uses neutron out-scattering to identify the existence of certain elements that are present in the object being examined. The device includes an accelerator which produces monoenergetic low energy fast neutrons at several specific energies, and detectors which measure monoenergetic neutrons which have passed unscattered through the object of interest. The object to be scanned is positioned between the accelerator and the detecting device. Neutrons that pass through the object unscattered are detected by the device.

In carrying out this invention, monoenergetic neutron beams at several specific energies are directed onto the object to be examined. At these low energies and with appropriately chosen neutron production targets, each angle of the neutron beam produced at the target corresponds to a particular neutron energy. The detectors, present at specific angles corresponding to the neutron energies of large resonances (peaks) in the total neutron cross sections of the elements being detected, measure the number of neutrons that pass through the object unscattered. If large amounts of an element are present in some part of the object, the nuclei of that element will scatter neutrons traveling at the specified energy and thus fewer neutrons will pass unscattered through that part of the object being examined. The device compares the number of neutrons which enter the object versus the number of the neutrons that exit the remote side and are detected by the device. What is being measured is thus the inclusive removal of neutrons of specified energies from their initial energy and direction by all nuclear processes by the material (elements) inside the object. Based on this information, a computer connected to the detectors can first calculate the density of the elements being detected along the path of the unscattered neutrons, and then, based on this information for all the measurements taken along different paths though the object of interest, a computer connected to the detectors can then perform the calculations for tomographic unfolding. This provides a "picture" of the densities of specified elements in the object of interest. Furthermore, the computer can provide an integrated measure of nitrogen and oxygen densities across different planes in the bag, as well as the entire bag, in order to detect substances in thin sheet form.

BRIEF DESCRIPTION OF THE DRAWINGS

The invention will be described in greater detail with the aid of the following figures.

DETAILED DESCRIPTION OF THE INVENTION

Physical Principles

Figure 1:
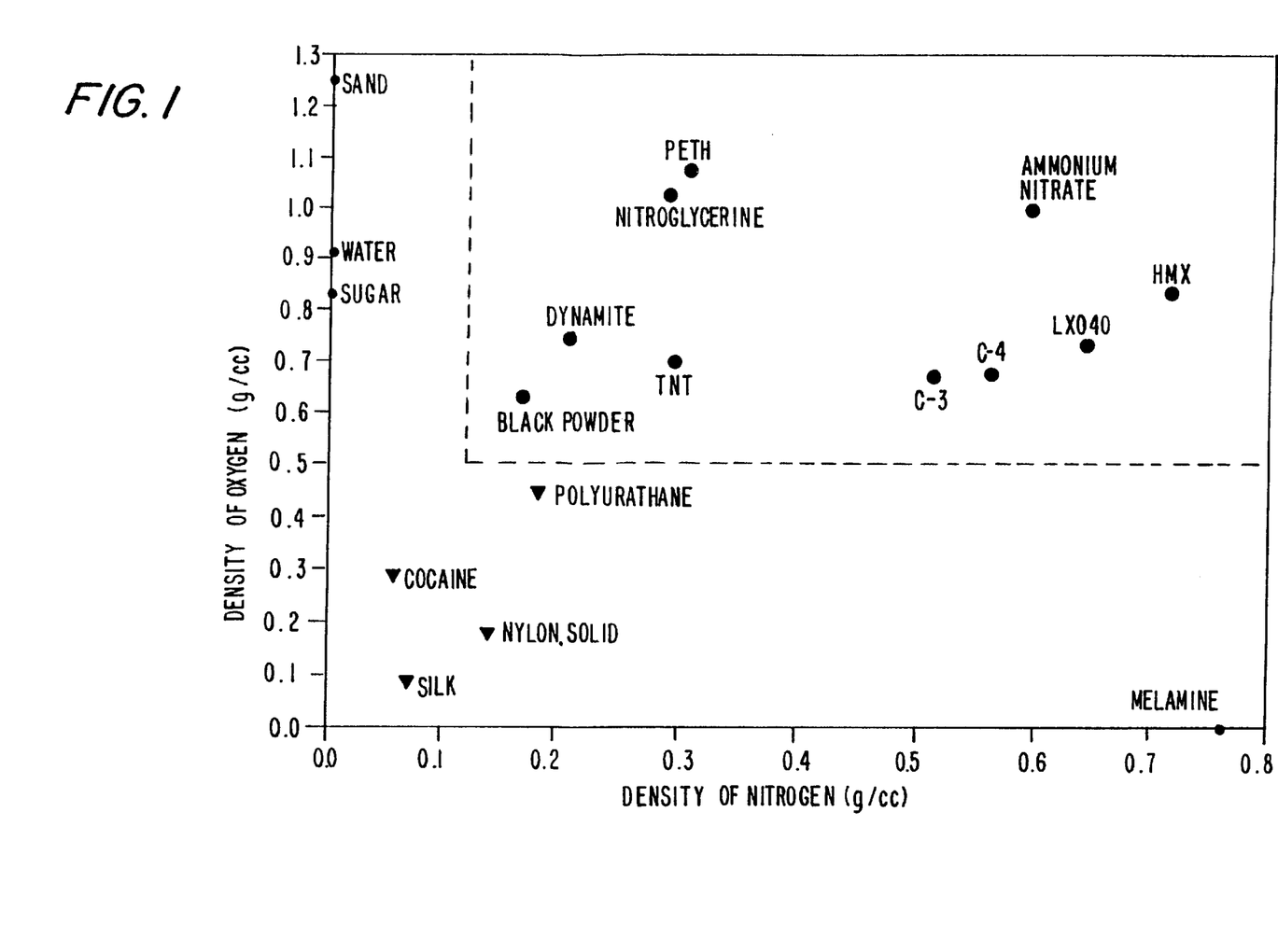
FIG. 1 is a scatter-plot of densities of oxygen and nitrogen in various materials, including explosives.

In order to detect concealed explosives in aircraft luggage or elsewhere, it is necessary to determine that a "fingerprint" or "signature" of that explosive is present. As discussed above, explosives characteristically contain high amounts of oxygen and nitrogen. High densities of both these elements are a good indicator that an explosive is present and thus constitute an explosive "fingerprint". FIG. 1 is a scatter-plot of densities of oxygen and nitrogen in various materials, including explosives. A high density of both nitrogen and oxygen is a strong indicator that an explosive is present and minimizes false positives and false negatives which often result when detecting only one element or, more generally, only one parameter.

Figure 2:
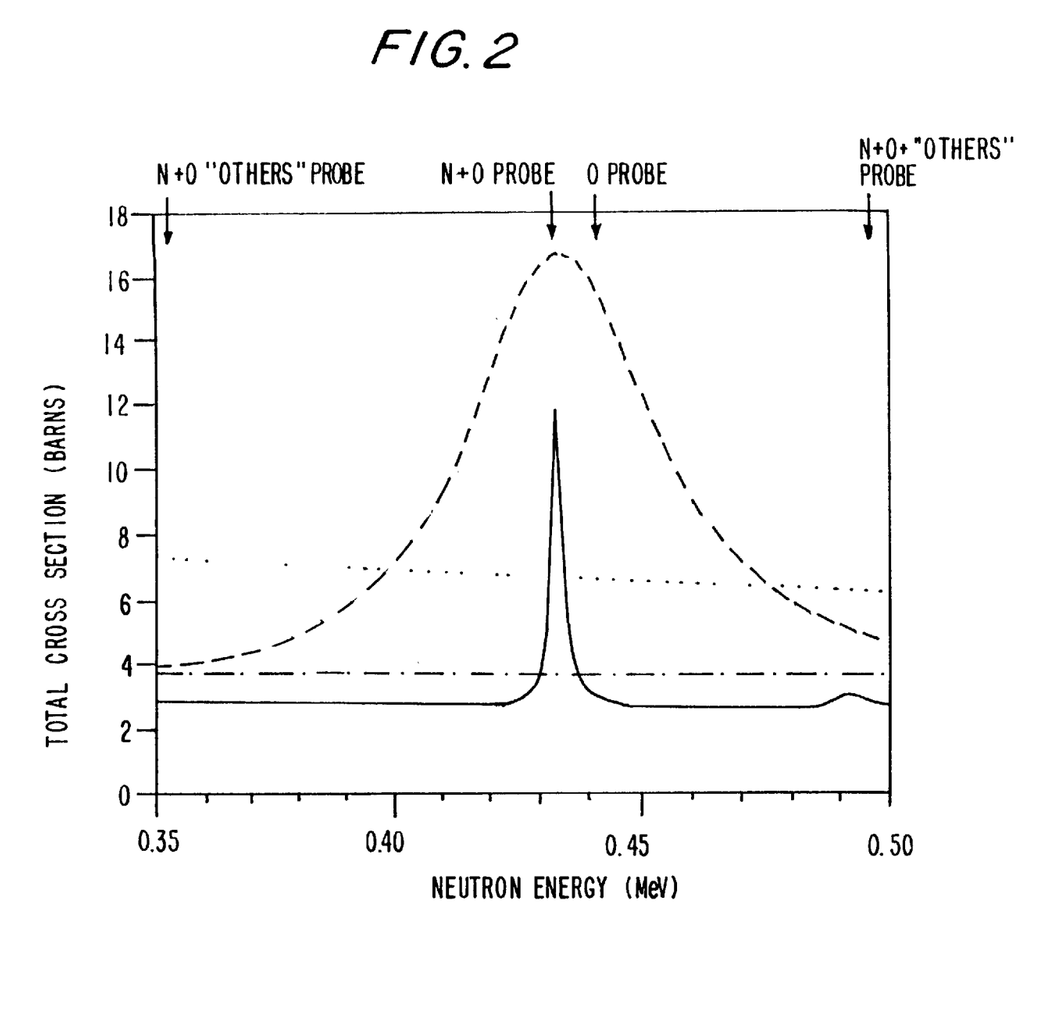
FIG. 2 is total neutron cross sections for different elements in the energy range from 0.3 to 0.5 MeV. The full curve is nitrogen, showing a narrow resonance. The dashed curve is oxygen, showing a broad resonance. The dotted curve is hydrogen and the dot-dash curve is carbon.

This invention takes advantage of the principle that elements, such as nitrogen and oxygen, preferentially scatter neutrons having specific energies. FIG. 2 illustrates the total neutron cross sections (interaction probabilities) for different elements in the energy range of 0.3 to 0.5 MeV (300 to 500 keV). As shown in this figure, there is a neutron energy region around 433.6 keV which features a large narrow nitrogen resonance and a large, much broader oxygen resonance. While the oxygen resonance has been known for years, the height of the nitrogen resonance is a fairly recent finding as illustrated in Harvey et al., *Proc. Conf. on Nuclear Data for Science and Technology*, pp. 729–31 (1992). Probing the target with 433.6 keV (±0.4%) incident neutrons samples primarily the line integrated nitrogen and oxygen density. Simultaneously probing with neutrons corresponding to approximately 442 keV (which is off the nitrogen resonance, but still in the oxygen resonance) samples primarily the line-integrated oxygen density. Probing the object with neutron energies corresponding to at or about 350 keV and 500 keV, which are off the nitrogen and oxygen resonances, samples primarily all other elements, such as hydrogen and carbon.

This invention also takes advantage of the principle that low neutron energy spectra produced by low-energy protons impinging on certain thin targets, such as lithium or tritium, have specific and identifiable angle-energy relationships. At these low neutron energies, each radial angle of the neutron beam corresponds to a particular and specific neutron energy. This angle-energy correlation can be used to isolate those radial angles that uniquely contain those energy neutrons that will best sample the nitrogen and/or oxygen densities (or the densities of any other element being sought) of the object being examined. For example, by probing the target with neutrons at the radial angle which contains 433.6 keV (±0.4%) incident neutrons, the line integrated nitrogen and oxygen densities are measured. Similarly, probing with neutrons at a slightly smaller angle (by ~0.80°) corresponding to approximately 442 keV, samples primarily the line integrated oxygen density. There are computer programs and tables, such as those described in Bengtsson et al., *Hth. Phys.* 18:577–578 (1970), and Liskien and Paulsen, *Nuc. Data Tables* 11: 569–619 (1973) and *Atomic Data and Nuclear Data Tables* 15: 57–84 (1975), which together provide the neutron energies and the corresponding neutron emission angle for different energy proton beams incident on different targets.

The Apparatus

Figure 3:
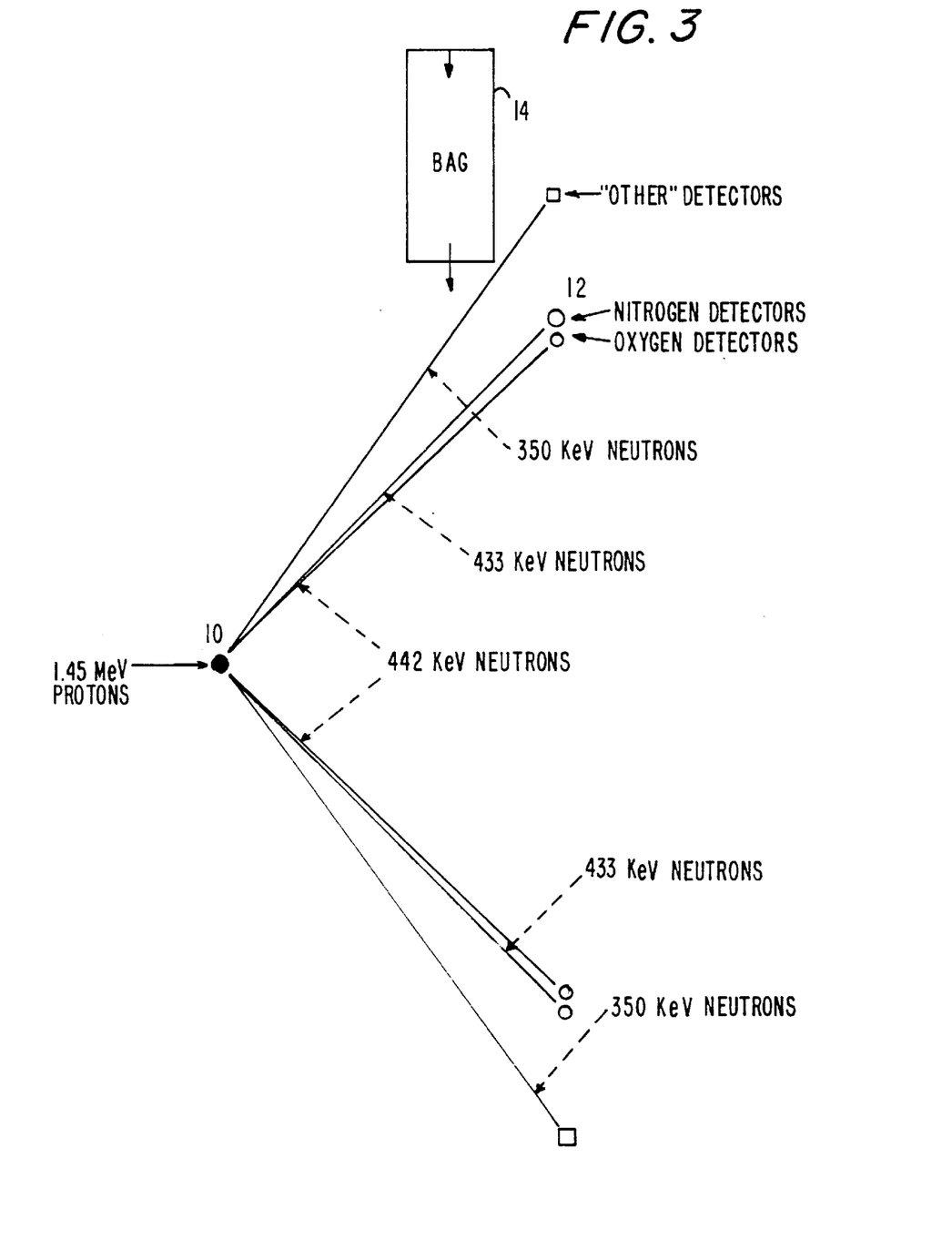
FIG. 3 is a schematic top view of the arrangement of the apparatus. Neutrons of a given energy are emitted in cone shapes at a given angle around the proton beam axis. Detectors are placed at the appropriate angles for each neutron energy. For clarity, only three neutron energies and corresponding detectors sets are shown.
Figure 4:
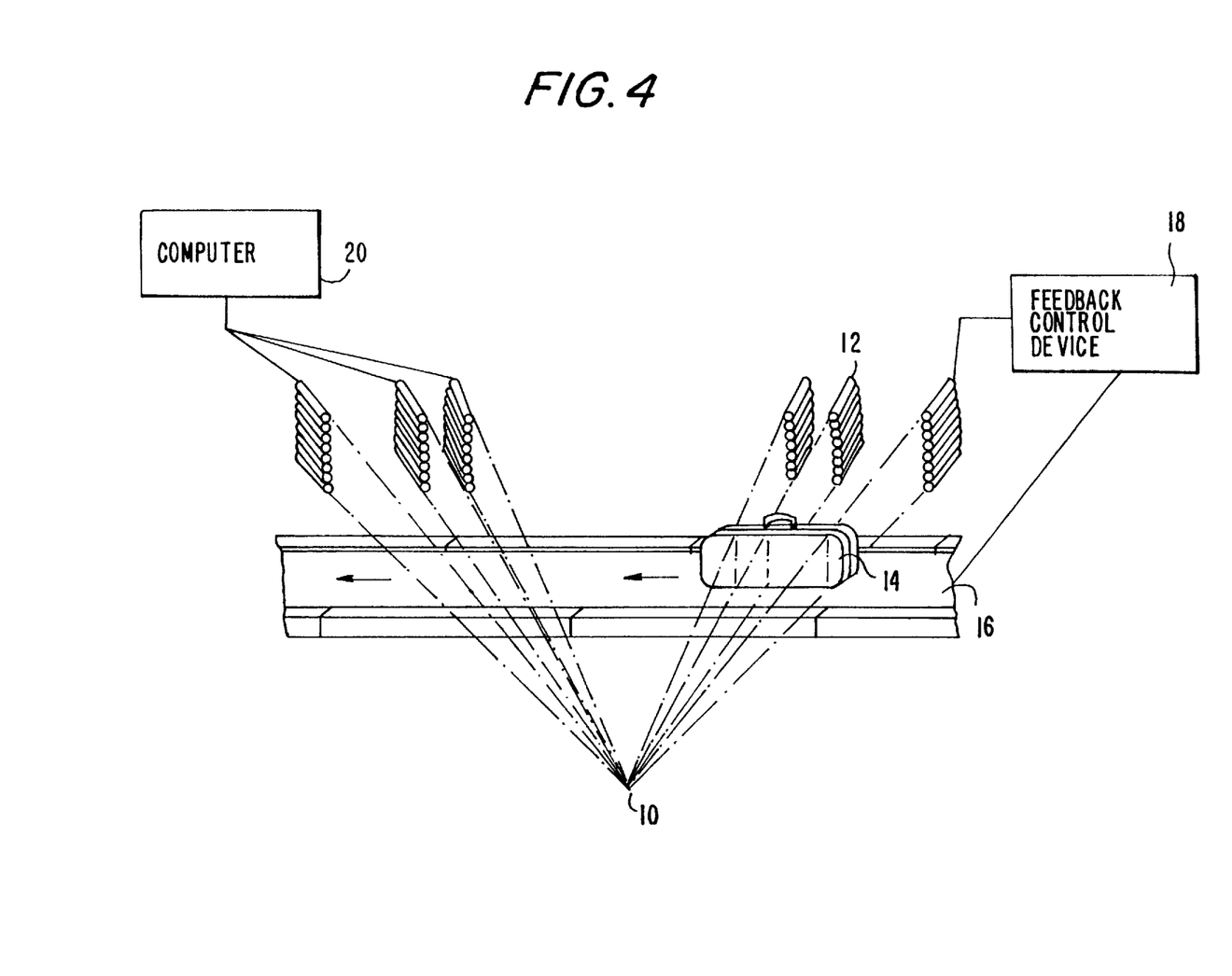
FIG. 4 is a schematic side view of the arrangements of the apparatus. Each level of shading corresponds to a different energy neutron beam, each pair of which are segments of conically shaped beams. For clarity, only three neutron energies and corresponding detector sets are shown.

The present inventions relates to an explosive detector system that uses neutron scattering to identify the existence of particular elements, such as nitrogen and oxygen. Referring to FIGS. 3 and 4, the device includes an accelerator and target (10) which produces a low-energy fast neutron spectrum and detectors (12) which measure the neutrons passing unscattered through the object of interest (14). The detectors are placed at specific angles relative to the neutron beam corresponding to the nitrogen and/or oxygen resonance energies. The object to be scanned is positioned between the accelerator and the detecting devices using, for example, a moving conveyor belt (16). The apparatus can also include a feedback control device (18) which is connected to the detectors. Once the detectors acquire a preset number of counts, a signal can be sent to the conveyor belt causing it to move the object to the next scanning position. A computer (20) can be connected to the detectors to analyze the line scans and to compute tomographic reconstruction.

The Accelerator

This detector system requires the use of an accelerator that produces low energy, monoenergetic fast neutrons in the range of about 0.35 to about 0.5 MeV. The monoenergetic neutrons are typically generated by impacting a target material with a beam of protons. By controlling the accelerating voltage, the energy of the emitted neutrons may be selected. Thus, the low neutron energies of at or about 0.35 MeV to about 0.5 MeV require only a very low energy proton beam (less than about 1.5 MeV) for the neutron generating reaction. This allows for an inexpensive, small, and reliable direct current (DC) accelerator, based, for example, on a cascade rectifier such as the Crockcroft-Walton machine, to be used. It is also possible that electrostatic accelerators, such as the Pelletron, (as described in Herb, IEEE Trans. Nucl. Sci. NS18: 71 (1971)) could be used.

All such accelerator systems, such as the Crockcroft-Walton accelerator, as described in Crockcroft and Walton, *Proc. Roy. Soc. A* 136:619 (1932), include an ion source, an accelerating tube, a method of generating high voltages for application to the electrodes of the accelerating tube, and an analyzing system for selecting ions of a particular type after acceleration. Recent implementations of the cascade rectifier (Crockcroft-Walton) principle include the nested high voltage generator, as described in Adler et al., Proc. SPIE Int. Soc. Opt. Eng. 2374: 194 (1995) and the tandem cascade accelerator as described in Yanch et al., Med. Phys. 19, 709 (1992).

An important development in the use of these accelerators is the tandem principle. A tandem accelerator contains two insulating columns. A high voltage terminal at their junction is charged positively within one column. A negative ion source supplies a beam of negative ions to the first accelerating tube. These ions are accelerated to the central terminal where they are stripped of electrons and converted to positive ions. The positive ions then enter the second accelerating tube in which they receive a second increment of velocity. The protons that emerge contain twice the terminal voltage. Thus, a power supply of about 0.75 MeV can produce a proton beam of about 1.5 MeV.

The monoenergetic neutrons are produced by bombarding a suitable thin low atomic number target, such as lithium or tritium, with these accelerated protons. When the protons strike the target, the protons impinge on the nuclei of this target and cause a reaction resulting in the emission of neutrons. In this case, the energy of the neutron emitted at any given radial angle is directly related to the incident energy of the proton.

The thickness of the tritium or lithium target material is directly related to the number of neutrons and the monoenergetic nature of the neutrons that are being produced. If the target material is thick, the neutron yield is greater, but the monoenergetic nature of the beam decreases. If the target is thin, the neutrons are more monoenergetic, but the neutron yield is smaller. Thus, one must balance yield versus the monoenergetic nature of the neutrons when choosing the thickness of the target material with the constraint that the energy width of the 433.6 keV neutron beam should not be much more than about ±0.4%.

This accelerator produces a spectrum of low energy fast neutrons, which, at any given angle, are monoenergetic. At these low energies, each radial angle of the spectrum corresponds to a particular neutron energy. In addition, by producing these low energy neutrons (less than 0.5 MeV) with an appropriate energy proton beam (less than 1.5 MeV), neutrons of the desired energy are uniquely produced in the shape of cones, the axes of which are parallel to the proton beam axis. By passing the object of interest through the beam, such as by using a conveyor belt, the object will contact the beam corresponding to a particular neutron energy level twice, but in mutually approximately perpendicular directions. This leads to better results for the subsequent tomographic reconstruction.

Those neutrons that emanate from the accelerator apparatus in the directions other than towards the detectors can be shielded using plastic or boronated substances. The hydrogen atoms in the plastic interact with the neutrons so that the neutrons are rapidly moderated inside the plastic (losing about two-thirds of their energy per interaction) and then get absorbed by the hydrogen or boron atoms in the plastic material. The walls of the room containing the detection device also generally contain a plastic shield material. Plastics such as polyethylene or borated polyethylene are generally used. Due to the use of low energy proton beams and low energy fast neutrons, minimal protective shielding is required.

The Detectors

Detector devices are used to measure the number of neutrons of specific energies that penetrate and pass unscattered through the scanned object. These detectors are gas-filled chambers, operating in the ion-chamber or proportional-counter modes, filled with specific gases that are especially sensitive to neutrons of specific energies and can therefore be used to detect the number of a particular element in the path of the neutron of that specific energy. In its simplest form, the ionization chamber is a gas-filled metal vessel into which is inserted an insulated electrode. Under the influence of ionizing radiation, the application of a potential difference of a few hundred volts causes a current flow through the gas. The neutrons that hit the ion chamber detector gas cause electrons to be removed from the atoms in the gas (ionizations). The electrons then move toward the positive voltage and cause a current to flow. A meter, attached to the detector, measures the electrical flow which is related to the number of neutrons hitting the device.

By changing the voltage which is applied to the counter, such detectors can also be operated in the proportional-counter mode, where the signal recorded is proportional to the number of ionization that are produced. This allows improved discrimination between signal and noise.

The detector with the best response for neutrons of the appropriate energy for probing a resonance of a particular element is one whose detection volume consists of that same element. Thus, each detector contains a gas which corresponds to the resonance being measured. Such a detector has a much reduced sensitivity to scattered "background" neutrons of different energies.

The detectors are placed at the appropriate radial angles relative to the incident proton beam direction, corresponding to specific neutron energies, so that specific elements can be measured. For example, the detector being used to measure the amount of oxygen in the object is placed at the angle corresponding to the neutron energy of the oxygen resonance. Furthermore, that detector contains oxygen gas in its chamber so that it efficiently detects any neutrons of that energy which passed through the suitcase or object.

The detectors are stacked so as to probe the vertical dimension of the object being examined. The detectors are not stacked directly on top of each other but are stacked so that they remain in line with the conical shaped neutron beam passing through the object being examined. The area of the detector determines the thickness of the line scans and thus the amount of the object that is being scanned at any one time. This detector area can be varied depending on the spatial resolution requirements of the system.

By placing these neutron detectors at appropriate radial angles relative to the initial beam direction, excellent energy resolution can be achieved, limited only by the area of the detector. As an example, a 20 mm diameter detector at 2 m from the neutron source yields an energy resolution better than 1%. This arrangement allows for simultaneous probing of different regions of the target bag with different energy neutrons.

The detectors can be connected to a computer which interprets the information and performs the calculations needed for tomographic reconstruction.

The Conveyor Belt

The object or suitcase to be scanned is positioned on a conveyor belt (or any other holding device) between the accelerator and the detectors. The conveyor belt is positioned so that the neutrons can penetrate the object and either be scattered by the nuclei or pass through the object to the detectors.

The conveyor belt moves the object in front of the neutron beam so that it is multiply line-scanned by neutrons of each energy. The line scans are taken in two near perpendicular directions due to the conical nature of the neutron beams.

As stated above, each scan of the object by specific energy neutron beams samples a projected area which corresponds to the area of the detector. Thus, the number of scans to sample the entire bag is determined by the area of the detector. The object will be in each scan location for a few hundredths of a second.

The amount of time that the neutron beam scans each portion of the object can be modified according to the number of neutrons passing through the object and reaching the detectors by a feedback control device. Thus, the motion of the conveyor belt can be controlled by a feedback mechanism which is connected to the detectors. Once the detectors acquire a preset number of counts, a signal can be sent to the conveyor belt causing it to move the object to the next scanning position. Thus, as more target elements (such as nitrogen and oxygen) are present in the object, fewer neutrons will reach the detector and the suitcase will remain in that position longer. This will allow a more extensive analysis of those areas where high densities of elements of interest are detected.

The Method

In carrying out this invention, a monoenergetic beam of protons is directed at a target to produce monoenergetic low energy, fast neutron beams, with different radial angles corresponding to specific neutron energies. The object of interest is irradiated by low energy, monoenergetic neutron beams of known intensity. Detectors, placed at the appropriate radial angles corresponding to the energies of the oxygen and nitrogen neutron resonances, as well as off these resonances, measure the neutrons that pass through the object unabsorbed and unscattered. The object being studied is moved on a conveyor belt transverse to the neutron beam axis. The object is moved at such a rate so that each neutron energy spectrum scans the object at approximately millimeter intervals. A computer is connected to the detectors to analyze and interpret the results of the orthogonal line scans and to compute the tomographic reconstruction.

EXAMPLE 1

In order to assess the potential to use the ~434 keV neutron scattering resonances in oxygen and nitrogen as a basis for an explosive detection system, a series of preliminary neutron transport computer simulations are performed. From the results, it is determined that, using these resonances, a clear "fingerprint" is seen for the presence of relatively small amounts of explosives, relative to other materials.

The Los Alamos neutron/photon transport code MCNP (Briesmeister J., *Los Alamos National laboratory Report* LA-12625-M (1933)) is used with cross sectional data taken from the current version of ENDF/B-VI.

The simulation consists of three elements, as depicted in FIG. 3: the neutron source, the absorber representing potential suitcase materials, and the detectors. The source term includes the angular variation of the outgoing neutron energy for the $^3$H(p,n) reaction at 1.443 MeV incident proton energy. This proton energy produces 433.6 keV neutrons (nitrogen resonant) at 45° relative to the initial proton beam direction. The proton energy and subsequent neutron beam energy and angles are derived from calculations based on Liskien and Paulsen, *Nucl. Data Tables* 11: 569–619 (1973).

Four spherical shells containing oxygen, nitrogen, polyethylene, and RDX explosive are simulated at locations between the source and the detectors (to simulate luggage contents).

In this simulation, detectors (10 mm in diameter) are placed radially at the appropriate angles to intercept 433.6, 442, and 500 keV neutrons, with their axes pointing towards the neutron source. These neutron energies respectively correspond to an energy on the nitrogen and oxygen resonances, an energy on the oxygen resonance only, and an energy higher than both oxygen and nitrogen resonances. The detectors have a sensitive detection volume consisting of nitrogen gas, oxygen gas, and deuterium gas, respectively.

In this simulation, the process is duplicated ten times at 36° intervals around the axis of the proton beam, in order to provide improved statistics. The simulations are run for $10^8$ neutron histories, leading to typical statistical errors of around 10%, and take about 16 hours to run on a 133 MHz Pentium computer.

FIGS. 6(A–D) shows the relative responses of the different detectors. The response of the three detectors relative to each other is very different for each of the four attenuators used. The RDX explosive shows a characteristic separation between the response of the three detectors which is a "fingerprint" of an absorber with both high nitrogen and high oxygen content. Furthermore, this simulation shows that distinctive fingerprints are clear using a relatively small number of neutrons to detect a relatively small amount (less than 10 gm/cm$^2$) of explosive.

EXAMPLE 2

Using the method of the instant invention, a low energy 1.45 MeV proton beam, incident on a thin tritium target, produces 433.6 keV neutrons on the surface of a 90° forward cone. It also produces 442 keV neutrons on a 88° forward cone, 350 keV neutrons on a 113° forward cone, and 500 keV neutrons on a 71° forward cone. Energy specific detectors are located at these angles to detect unscattered neutrons of the appropriate energy which have passed through the bag. FIG. 3 is a schematic top view and FIG. 4 is a schematic side view of this arrangement. For clarity only three neutron energies and corresponding detector sets are shown. In practice, there may be one more energy (~500 keV) detected at an appropriate angle.

Neutrons of a given energy are emitted on cones of a given angle around the proton beam axis. Each level of shading in FIG. 4 corresponds to a different energy neutron beam, each pair of which are segments of a conically shaped beam.

Figure 5:
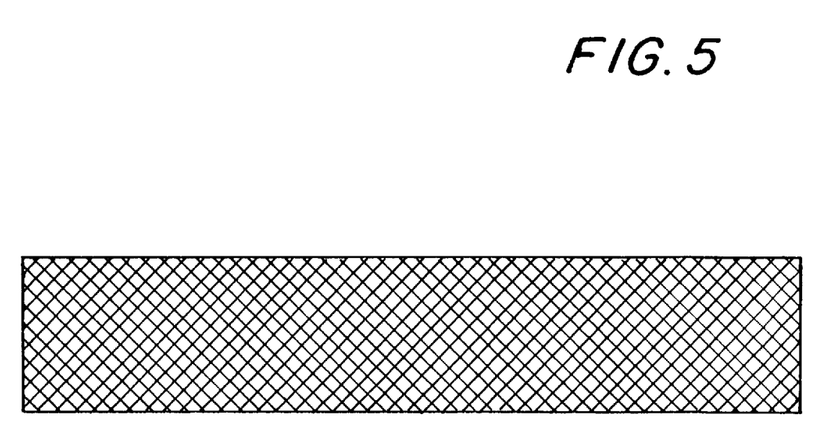
FIG. 5 is a schematic of near-orthogonal line probes across a suitcase (single slice, top view). Each line, which is about 10 mm broad and separated from the next line by about 5 mm, corresponds to separate attenuation measurements of neutron energies of 433.6, 442, 350, and 500 keV.
Figure 6A:
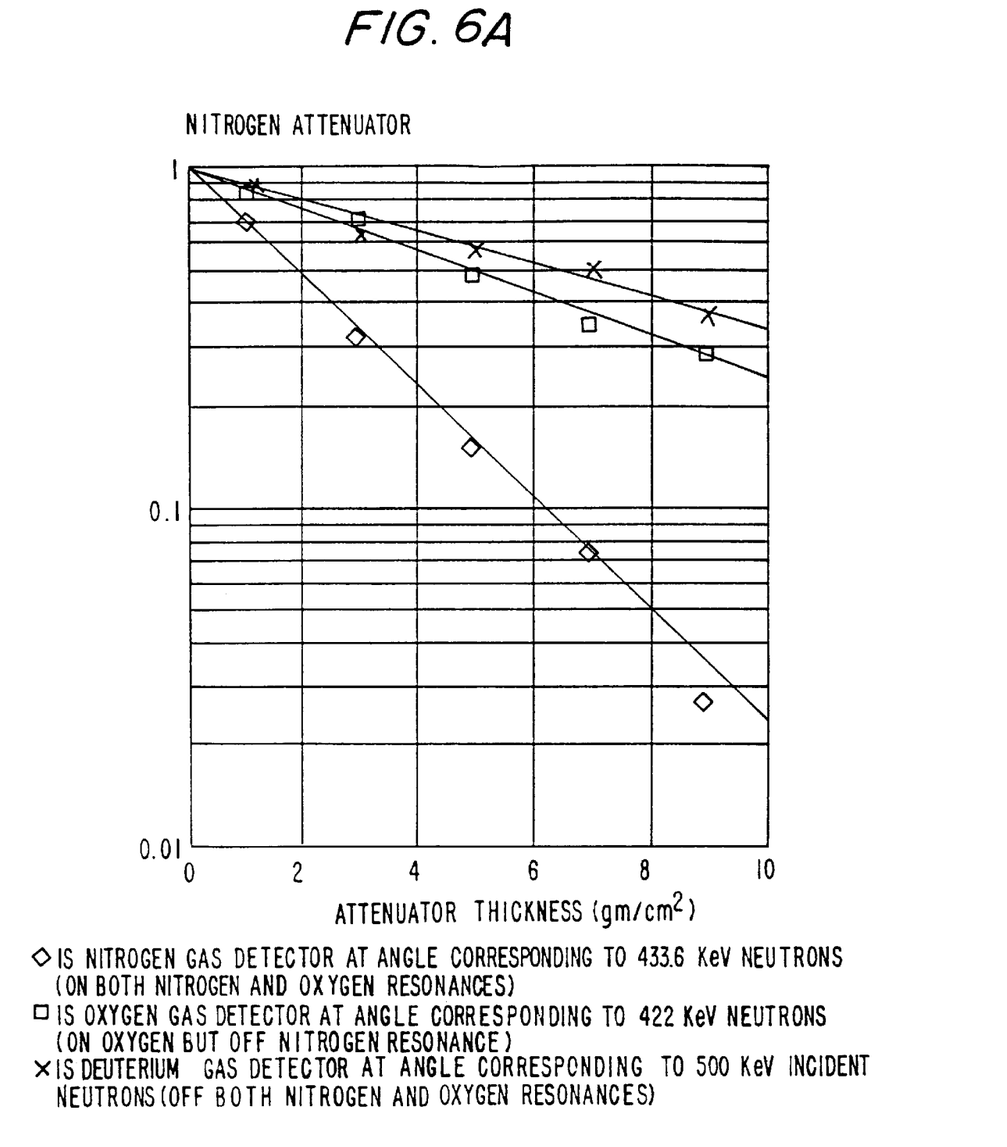
FIG. 6A–D depict the results of a computer simulation (using the neutron transport code MCNP) of normalized ionization chamber response versus density of absorber (object of interest) for three detectors. ◊ is from a nitrogen gas detector at the angle corresponding to 433.6 keV neutrons (on both nitrogen and oxygen resonances), ☐ is from an oxygen gas detector at the angle corresponding to 442 keV neutrons (on oxygen but off nitrogen resonance), and X is from a deuterium gas detector at the angle corresponding to 500 keV incident neutrons (off both nitrogen and oxygen resonances).
Figure 6B:
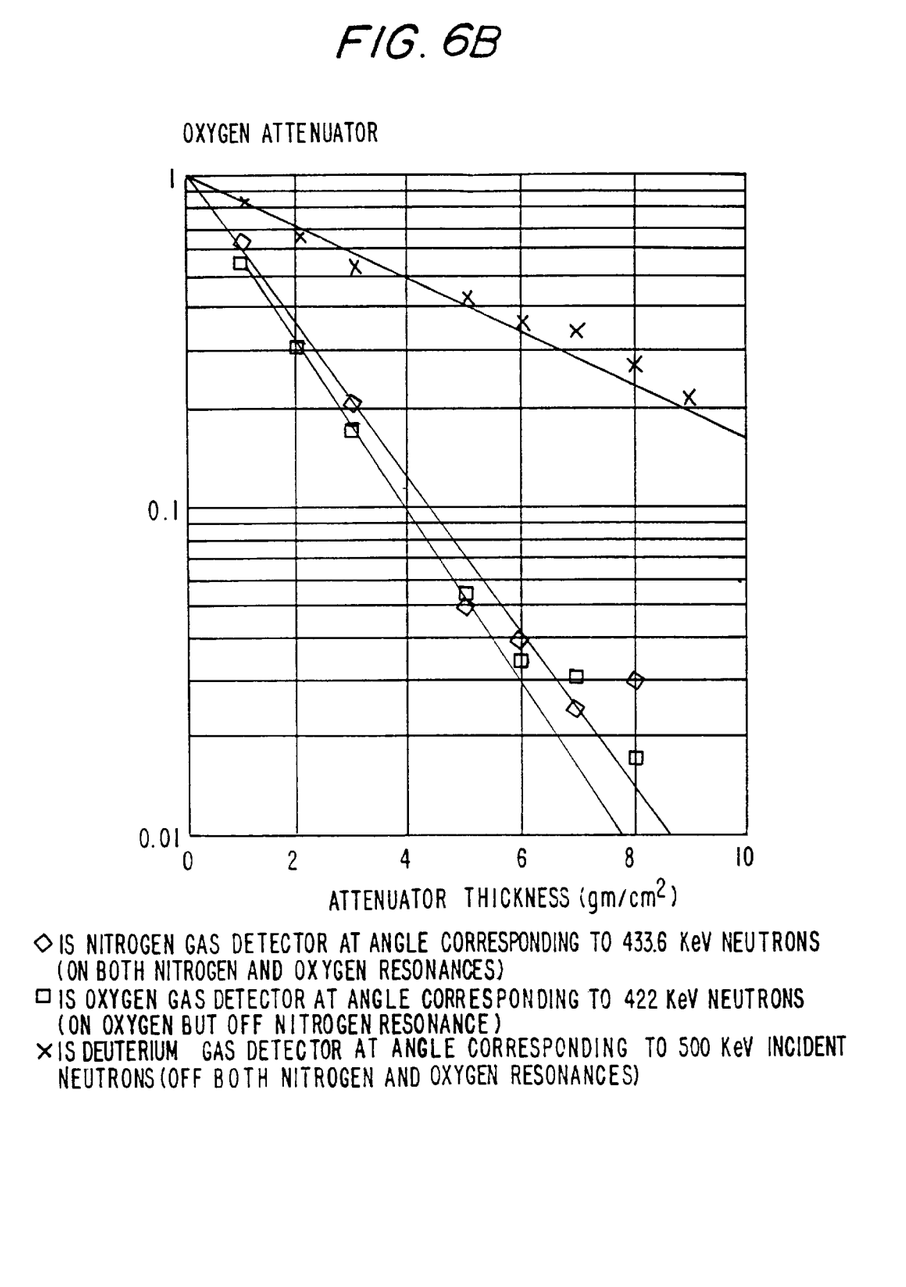
Figure 6C:
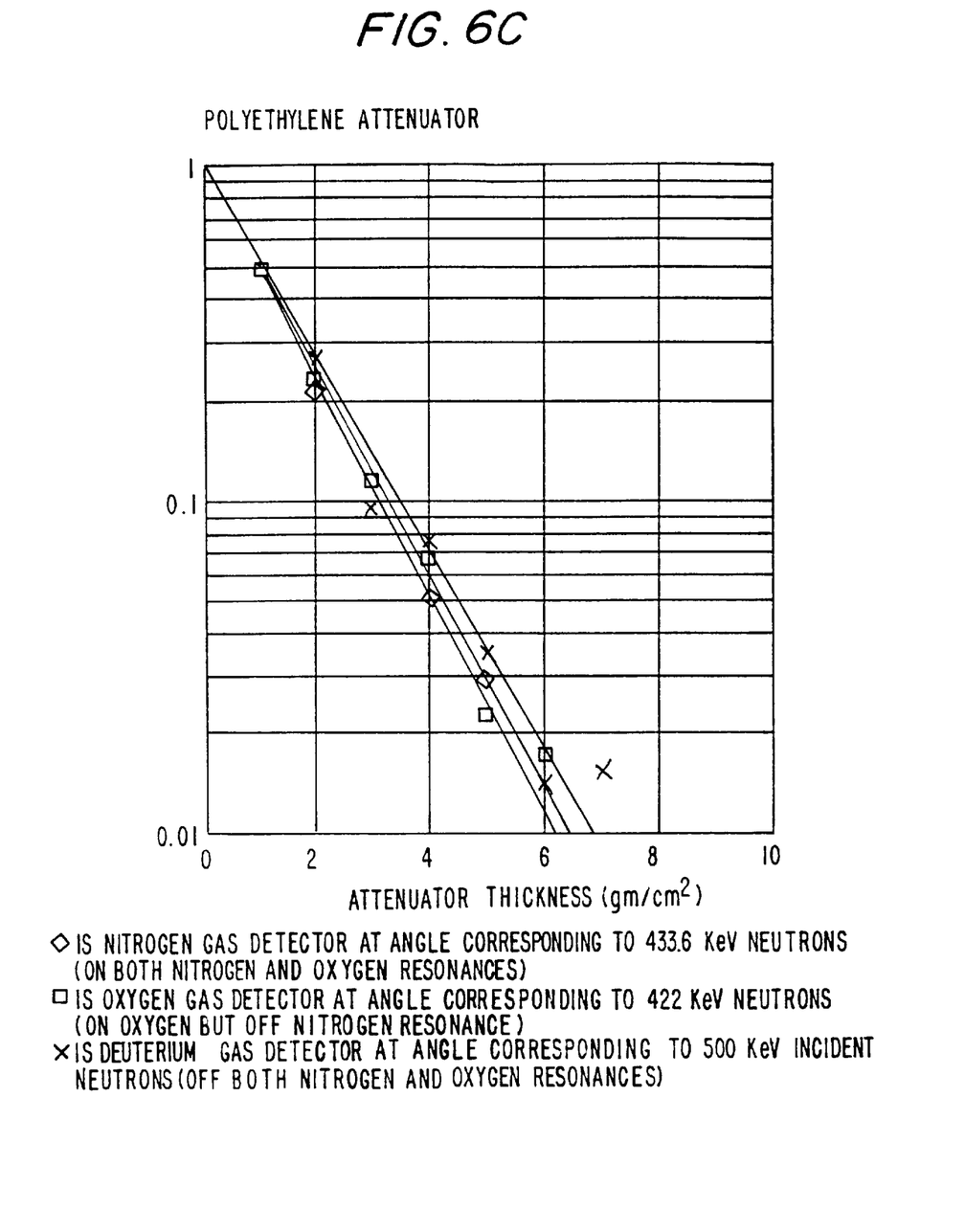
Figure 6D:
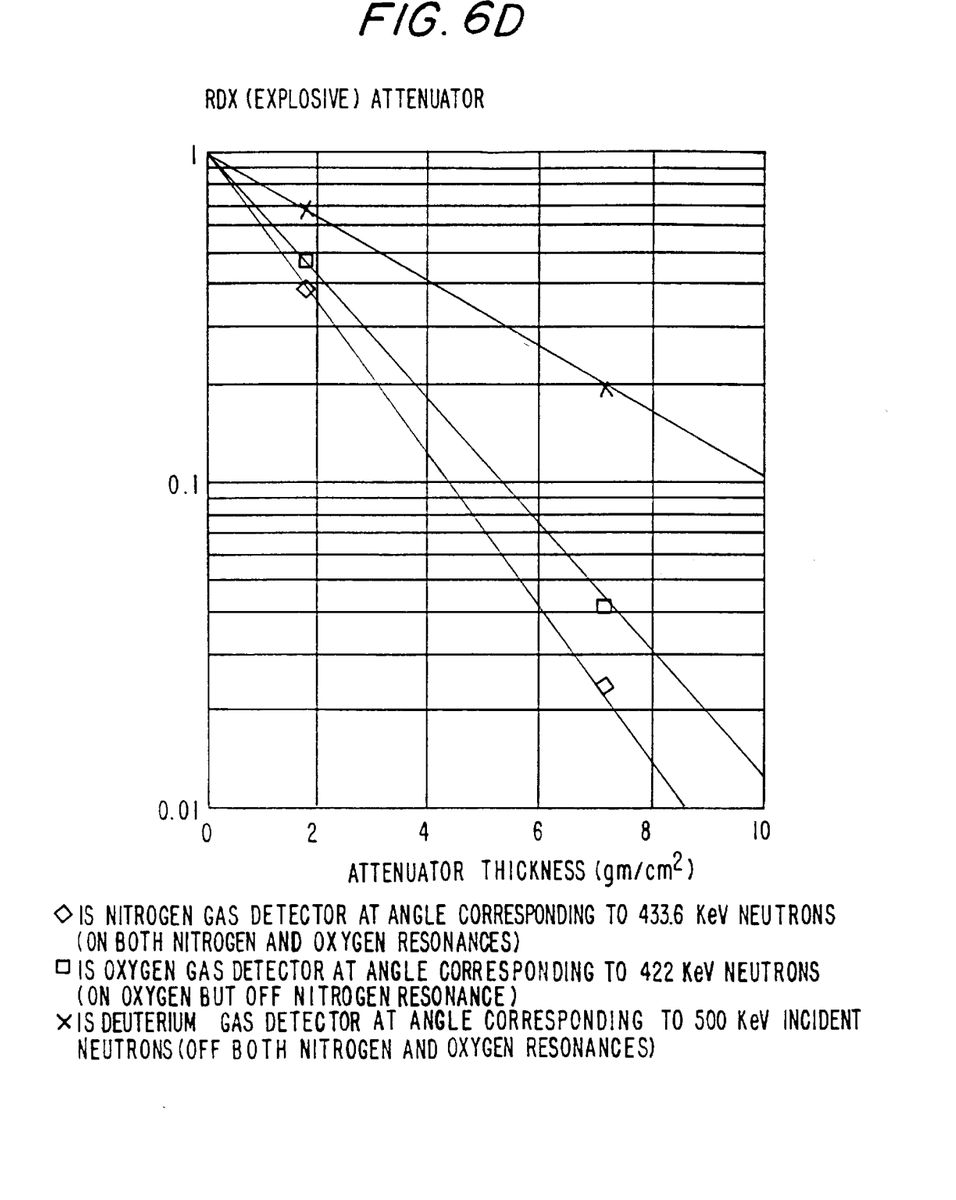

The suitcase is linearly transported across the cones, resulting in two near-perpendicular scans for each desired neutron energy. FIG. 5 is a schematic of a two-dimensional representation of these near orthogonal line probes across the bag. Each line corresponds to separate attenuation measurements at neutron energies of 433.6, 442, 350, and 500 keV. The lines correspond to the area of the appropriate detector, which is about 10 mm broad. Each line is separated from the next line by about 5 mm.

Vertically stacked banks of detectors, containing the appropriate material, are placed at the appropriate angle for each energy. The 442 keV neutrons are probing line-integrated oxygen densities. Two banks of ion-chamber detectors, whose sensitive volumes are made of oxygen gas, are located at the appropriate angles (at or about 44° from the incident proton beam direction). For the 442 keV neutrons, the detectors are long, thin ion chambers, filled with oxygen gas, whose axes point toward the neutron source. The detectors are stacked one on top of each other to allow scanning of the full height of the object as in FIG. 4.

Similarly, for the 433.6 keV neutrons, which are probing line-integrated nitrogen and oxygen densities, a similar geometry of detectors are used, but at the appropriate radial angles (at or about 45° from the incident proton beam direction). The ion chamber detectors are filled with nitrogen gas.

In a similar fashion, the 350 and 500 keV neutron detectors, probing line-integrated "all other element" densities, each consist of two vertical bank detectors located at the appropriate radial angles (at or about 56° and 36°, respectively). Here, the detection gas in the detectors is less important, so a standard detector gas such as deuterium or hydrogen is used.

As the object is moved across the neutron beams on the conveyor belt, it stays in a given position for a few hundredths of a second, during which the neutron attenuation is measured in each of the detectors (corresponding to attenuations at different neutron energies). Then the object moves about a centimeter, after which another set of measurements are taken. This continues for the length of the suitcase. Due to the conical shape of the neutron beams, two sets of scans are actually done, through lines in the bag that are roughly perpendicular to each other (FIG. 5).

For each line (L) through the bag in FIG. 5 which is probed with these different neutron energies, the local densities of each of the elements ($n_{L,Z}$) (Z=nitrogen, oxygen and "other elements") can be determined from the following two equations:

$$A_{LE} = \sum_{Z} N_{LZ}\, \sigma_{ZE} \qquad (1)$$

$$N_{LZ} = \int_{0}^{l} n_{LZ}(x)\, dx \qquad (2)$$

The attenuation of neutrons of energy E along line L ($A_{LE}$) is related to the proportion of neutrons that are scattered by the object being examined. The $A_{LE}$ quantity is directly related to what is measured by the detectors.

$\sigma_{ZE}$ is the total neutron cross section for the natural abundance of element Z at energy E. In other words, it is related to the ability of atoms of a given element (Z) to scatter or absorb neutrons whose energy is E. These $\sigma_{ZE}$ cross sections are known in the art and are determined by standard physics techniques.

$\sigma_{ZE}$ is known and $A_{LE}$ is measured from the detector readings. Thus $N_{LZ}$ can be obtained using the first equation by a rapid, simple least-square procedure, such as that suggested by Overley et al., *U.S. Dept. of Transportation/FAA Report DOT/FAA/CT-94/103* (1994). Again, $N_{LZ}$ is the total number of atoms of element Z along a given line L, running through the object.

The second equation can then be used to determine $n_{LZ}$ which is the density of an element (Z) at any given point (x) along a line L of length l in the object. Obtaining $n_{LZ}$ from $N_{LZ}$ is called tomographic reconstruction.

Once the $N_{LZ}$ values are obtained for many lines at different angles, a computer is used to "unfold" this information and calculate the densities of elements of interest at each location or voxel in the object. This tomographic reconstruction specifies those regions containing high nitrogen and oxygen contents. The computer tomography can be achieved with software and hardware customized for the necessary high-speed real-time inverse Radon transfer calculations and image reconstruction needed for tomographic reconstruction.

It is apparent from the above description that this novel method and apparatus for detecting explosions has significant advantages over the prior art methods of explosive detection. The use of low neutron energies (0.35 to 0.5 MeV) requires the use of a very low energy proton beam (<1.5 MeV) for the neutron generating reaction. This allows for a small, simple, and reliable accelerator system and for much reduced protective shielding. Because a small proton accelerator is required and because time-of-flight is not used, a small overall footprint is generated and the entire apparatus can fit in a very small room. The use of these neutron energies also minimizes the possibility of neutron activation.

The apparatus can detect explosives which are present in relatively small amounts (less than 10 gm/cm$^2$). Moreover, the technique of measuring unscattered monoenergetic neutrons exhibits excellent neutron energy resolution (<1%) leading to high sensitivity and specificity and produces spatial reconstructions of nitrogen and oxygen with enhanced spatial resolution, sensitivity and specificity.

In addition to detecting high densities of oxygen and nitrogen in explosives, other elements can be detected using this invention by modifying the neutron energy spectrum. For example, this invention can be used to identify the presence of drugs in concealed containers by detecting high densities of carbon and oxygen. When detecting the presence of carbon, neutron energies of on or about 2.1 MeV are needed.

The above description of the invention is intended to be illustrative and not limiting. Various changes or modifications in the embodiments described may occur to those skilled in the art. These can be made without departing from the spirit or scope of the invention. Accordingly, it is intended that the invention be limited only to the extent required by the claims and the applicable rules of law.

We claim:

1. An apparatus for detecting the presence of an element in an object, comprising:
    neutron source means for directing at least one substantially monoenergetic beam of neutrons onto the object, said neutrons having an energy;
    neutron detector means for detecting the neutrons from the monoenergetic beam of neutrons that pass unscattered through the object, the neutron detector means positioned at a radial angle relative to the neutron source means, which angle corresponds to the energy of the neutrons being detected;
    a means for positioning the object between the neutron source means and the neutron detector means; and
    a means for comparing a first number of neutrons emanating from the neutron source means to a second number of neutrons measured by the neutron detector means.

2. The apparatus as claimed in claim 1 further comprising a means for computing the density of an element in a particular area of the object, the computing means connected to the neutron detector means.

3. The apparatus, as claimed in claim 1, wherein the neutron source means provides a substantially monoenergetic beam of neutrons having an energy from about 0.35 to about 0.50 MeV.

4. The apparatus, as claimed in claim 1, wherein the neutron source means comprises a direct current accelerator and a target.

5. The apparatus, as claimed in claim 1, wherein the neutron detector means includes a feedback control device which activates the object positioning means upon the detection of a preset number of neutrons.

6. The apparatus, as claimed in claim 1, wherein the neutron detector means is stacked so as to probe the vertical dimension of the object being examined.

7. The apparatus, as claimed in claim 1, wherein the neutron detector means is a chamber containing a preselected element in gaseous form and operated in ion-chamber or proportional-counter mode.

8. The apparatus, as claimed in claim 7, wherein the preselected element is nitrogen, the neutron source means provides a substantially monoenergetic beam of neutrons having an energy of about 0.433 MeV, and the neutron detector means is placed at a radial angle corresponding to the direction of the beam of 0.433 MeV energy neutrons.

9. The apparatus, as claimed in claim 7, wherein the preselected element is oxygen, the neutron source means provides a substantially monoenergetic beam of neutrons having an energy of about 0.442 MeV, and the neutron detector means is placed at a radial angle corresponding to the direction of the beam of 0.442 MeV energy neutrons.

10. The apparatus, as claimed in claim 7, wherein the preselected element is deuterium gas, the neutron source means provides a substantially monoenergetic beam of neutrons having an energy of about 0.35 MeV, and the neutron detector is placed at a radical angle corresponding to the direction of the beam of 0.35 MeV energy neutrons.

11. The apparatus, as claimed in claim 7, wherein the preselected element is deuterium gas, the neutron source means provides a substantially monoenergetic beam of neutrons having an energy of about 0.50 MeV, and the neutron detector is placed at a radical angle corresponding to the direction of the beam of 0.50 energy neutrons.

12. An apparatus for detecting the presence of oxygen and nitrogen in a region of a container as a screening technique for determining the presence of an explosive, which comprises:

a direct current accelerator which impinges accelerated protons upon a target to produce substantially monoenergetic neutrons having energies of from about 0.35 to about 0.50 MeV;

a first gas-filled detector which measures the monoenergetic neutrons which pass unscattered through the container, the detector being positioned at a preselected angle corresponding to the direction of the neutrons of nitrogen resonance energy;

a second gas-filled detector which measures the monoenergetic neutrons which pass unscattered through the container, the detector being positioned at a preselected angle corresponding to the direction of the neutrons of oxygen resonance energy;

a third gas-filled detector which measures the monoenegetic neutrons which pass unscattered through the container, the detector being positioned at a preselected angle corresponding to the direction of the energy neutrons selected from the group consisting of about 0.35 MeV and about 0.50 MeV energy neutrons;

a means for positioning and moving the container between the direct current accelerator and the gas-filled detectors; and a computer connected to the gas-filled detectors for comparing a first number of neutrons emanating from the accelerator to a second number of neutrons measured by the gas-filled detectors to detect the presence of oxygen and nitrogen in a region within the container.

13. The apparatus, as claimed in claim 12, further comprising a fourth gas-filled detector which measures the monoenergetic neutrons which pass unscattered through the container, the detector being positioned at a preselected angle corresponding to the direction of the energy neutrons selected from the group consisting of about 0.35 MeV and about 0.50 MeV energy neutrons.

14. The apparatus, as claimed in claim 12, wherein the gas-filled detectors include a feedback control device which activates the container positioning means to move the container upon the detection of a preset number of neutrons.

15. The apparatus, as claimed in claim 12, further comprising a means for computing the density of an element in a particular area of the container, the computing means connected to the gas-filled detectors.

16. The apparatus, as claimed in claim 12, wherein the target is a low atomic number element selected from the group consisting of lithium and tritium.

17. The apparatus, as claimed in claim 12, wherein the direct current accelerator provides a substantially monoenergetic beam of neutrons having an energy of about 0.433 MeV, the first gas-filled detector is filled with nitrogen gas and the first gas-filled detector is placed at a radial angle corresponding to the direction of the beam of 0.433 MeV energy neutrons.

18. The apparatus, as claimed in claim 12, wherein the direct current accelerator provides a substantially monoenergetic beam of neutrons having an energy of about 0.442 MeV, the second gas-filled detector is filled with oxygen gas and the second gas-filled detector is placed at a radial angle corresponding to the direction of the beam of 0.442 MeV energy neutrons.

19. The apparatus, as claimed in claim 12, wherein the direct current accelerator provides a substantially monoenegetic beam of neutrons having an energy of approximately 0.35 MeV, the third gas-filled detector is filled with deuterium gas and the third gas-filled detector is placed at a radical angle corresponding to the direction of the beam of approximately 0.35 MeV energy neutrons.

20. The apparatus, as claimed in claim 12, wherein the direct current accelerator provides a substantially monoenergetic beam of neutrons having an energy of about 0.50 MeV, the third gas-filled detector is filled with deuterium gas and the third gas-filled detector is placed at a radical angle corresponding to the direction of the beam of approximately 0.50 MeV energy neutrons.

21. The apparatus, as claimed in claim 13, wherein the direct current accelerator provides substantially monoenergetic beams of neutrons having energies of approximately 0.35 and 0.50 MeV, the third gas-filled detector is filled with deuterium gas and is placed at a radical angle corresponding to the direction of the beam of approximately 0.35 MeV neutrons, and the fourth gas-filled detector is filled with deuterium gas and is placed at a radical angle corresponding to the direction of the beam of approximately 0.50 MeV neutrons.

22. A method for detecting the presence of a preselected element in an object, comprising the steps of:

providing a neutron source means which generates a substantially monoenergetic beam of neutrons;

directing the beam of neutrons onto the object;

providing a neutron detector means for detecting neutrons passing unscattered through the object, the detector being positioned downstream from the object at preselected radial angles relative to the neutron source means, corresponding to energy of the neutrons being detected;

positioning the object between the neutron source means and the neutron detector means; and comparing a first number of neutrons emanating from the neutron source means to a second number of neutrons detected by the neutron detector means.

23. The method, as claimed in claim 22, wherein the substantially monoenergetic beam of neutrons has an energy of from about 0.35 to about 0.50 MeV.

24. The method, as claimed in claim 22, further comprising the step of computing the density of an element in a particular area of the object.

25. A method for detecting the presence of oxygen and nitrogen in a region of a container as a screening technique for determining the presence of an explosive, which comprises the steps of:

providing a direct current accelerator which impinges accelerated protons upon a target to produce substantially monoenergetic neutrons having energies of from about 0.35 to 0.50 MeV;

directing monoenergetic beams of neutrons onto the container;

providing a first gas-filled detector, positioned at a preselected angle relative to the accelerator corresponding to the direction of a beam of monoenergetic neutrons of nitrogen resonance energy, which measures the monoenergetic neutrons which pass unscattered through the container;

providing a second gas-filled detector, positioned at a preselected angle relative to the accelerator corresponding to the direction of a beam of monoenergetic neutrons of oxygen resonance energy, which measures the monoenergetic neutrons which pass unscattered through the container;

providing a third gas-filled detector, positioned at a preselected angle relative to the accelerator corresponding to the direction of a beam of energy neutrons selected from the group consisting of about 0.35 MeV and about 0.50 MeV energy neutrons, which measures the monoenergetic neutrons which pass unscattered through the container;

positioning and moving the container between the accelerator and the gas-filled detector; and comparing a first number of neutrons emanating from the accelerator to a second number of neutrons detected by the gas-filled detectors to determine the presence of nitrogen and oxygen in a region of the container.

* * * * *